United States Patent [19]

Muehlenbein

[11] Patent Number: 5,038,489

[45] Date of Patent: Aug. 13, 1991

[54] POSTURE MEASURING INSTRUMENT

[75] Inventor: James A. Muehlenbein, Villa Park, Ill.

[73] Assignee: Novel Products, Inc., Addison, Ill.

[21] Appl. No.: 539,338

[22] Filed: Jun. 18, 1990

[51] Int. Cl.⁵ .................................................. G01B 1/00
[52] U.S. Cl. ........................................ 33/512; 33/277;
33/1 BB; 33/1 N; 33/391; 33/343
[58] Field of Search .............. 33/511, 512, 1 K, 1 BB,
33/1 B, 1 C, 276, 277, 283, 1 R, 1 N, 20.1, 20.3,
391, 340, 341, 343; 434/90, 91

[56]  References Cited

U.S. PATENT DOCUMENTS

| 449,681 | 4/1891 | Lasar | 33/277 |
| 1,415,833 | 5/1922 | Ginsburg | 33/277 X |
| 1,664,695 | 4/1928 | Masters | 33/391 |

FOREIGN PATENT DOCUMENTS

| 15752 | 3/1912 | Denmark | 33/277 |
| 440295 | 5/1912 | France | 33/343 |
| 542537 | 7/1941 | United Kingdom | 33/277 |

Primary Examiner—Harry N. Haroian
Attorney, Agent, or Firm—Wood, Phillips, Mason, Recktenwald & Vansanten

[57] ABSTRACT

A hand held instrument for determining the degree of angular deviation of a line between selected points on a subject from a gravity-dependent reference, including a transparent base through which the selected points may be viewed and a gravity-dependent indicator mounted on the base for free rotation under the influence of gravity. The base includes indicia complementary with the gravity-dependent indicator to provide an indication of the degree of deviation between the gravity-dependent indicator and the line between selected points on the subject when the instrument is held in a substantially upright position.

17 Claims, 1 Drawing Sheet

U.S. Patent     Aug. 13, 1991     5,038,489
Fig. 1
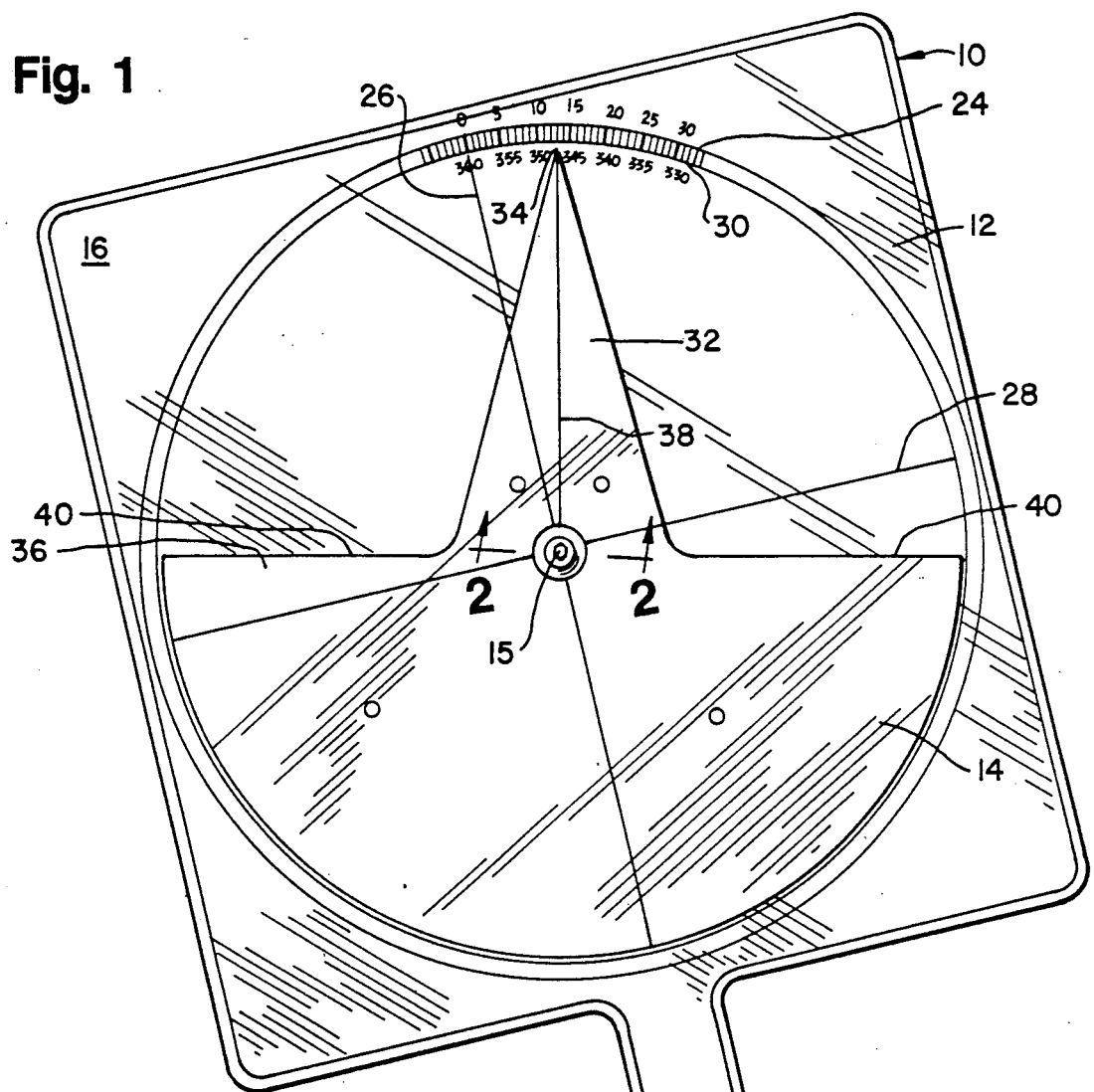
Fig. 2
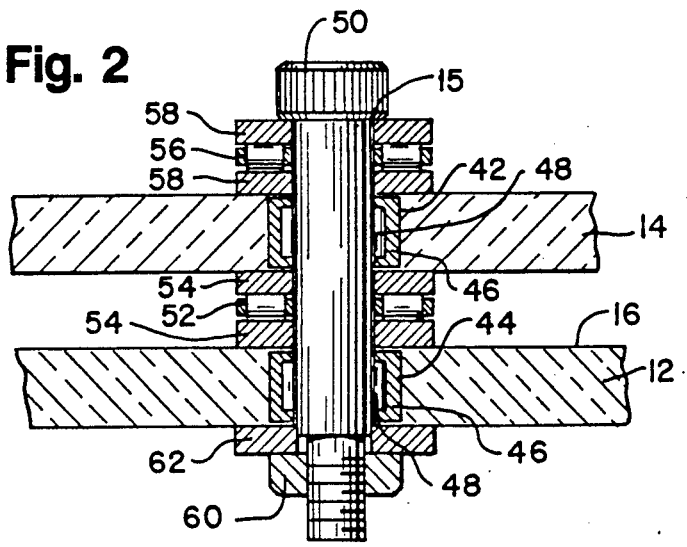
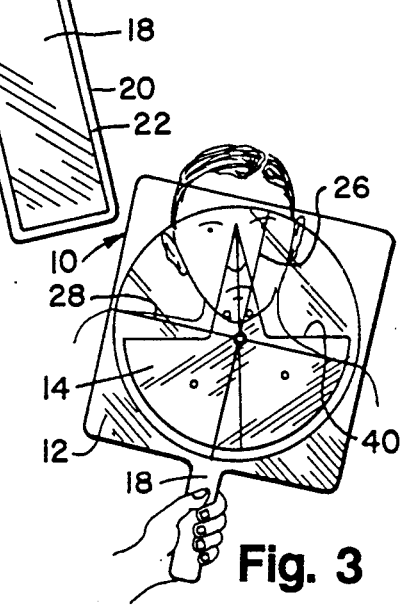
Fig. 3

POSTURE MEASURING INSTRUMENT

BACKGROUND OF THE INVENTION

1. Technical Field

The present invention relates to an instrument for determining the angular deviation of selected points on a subject from a selected reference. More particularly, the present invention discloses a hand-held instrument for determining such an angular deviation to evaluate the posture of human subjects, both stationary and in motion.

2. Background Art

Health care professionals have conducted posture analyses of subjects in the past to analyze posture factors such as spinal curvature, and the tilt of the head, shoulders, hips, and trunk. For example, when viewing a subject from the side, posture problems may manifest themselves as deviations from vertical by a line drawn from the middle ear, through the acromial process, to the middle hip, middle knee and middle ankle. Posture problems may also manifest themselves as deviation from horizontal by a line drawn through the right and left iliac crest of the hips, of a line drawn through the right and left acromial process or mid-shoulder, or of a line drawn between the ears.

Posture analyses have been conducted in the past using devices such as a grid provided on a sheet of transparent plexiglas suspended from a wall bracket or ceiling. Such grids are typically set in a fixed position with respect to true vertical when hung in place through use of a plumb-bob.

Portable posture analyzers have also been provided.

Still other devices have been provided for measuring the range of motion of the joints of the body; one such device includes a stabilizer bubble for accurate placement.

The prior art devices can, however, be expensive, provide only limited types of measurements, and/or be difficult and clumsy to use.

The present invention is directed toward overcoming one or more of the problems set forth above.

SUMMARY OF THE INVENTION

In one aspect of the present invention, a hand-held instrument for determining the degree of angular deviation of a line between selected points on a subject from a gravity-dependent reference is provided having a transparent base through which the selected points on the subject may be viewed, and a gravity-dependent indicator mounted on the base for free rotation under the influence of gravity. The base includes indicia complementary with the gravity-dependent indicator to provide an indication of the degree of deviation between the gravity-dependent indicator and the line between the selected points on the subject when the instrument is held in a substantially upright position.

In another aspect of the present invention, a method for determining the degree of deviation of a line between selected points on a subject from a gravity-dependent reference is disclosed, including providing a hand-held instrument as described above, holding the instrument in a substantially upright position, viewing selected points on the subject through the base of the instrument, aligning the reference line with the selected points on the subject, allowing the indicator to rotate to under the influence of gravity, and determining the deviation angle from the particular angle indicia aligned with the pointer.

It is an object of the present invention to provide an inexpensive instrument which may be simply and easily used to accurately analyze different angles on a body. It is another object of the invention to provide such an instrument for easily analyzing different aspects of the posture of individuals, both while stationary and in motion.

BRIEF DESCRIPTION OF THE DRAWINGS

FIG. 1 is a plan view of the instrument of the present invention;

FIG. 2 is a partial cross-sectional view, taken along line 2—2 of FIG. 1; and

FIG. 3 is a view of the instrument of the present invention in use, with a subject being viewed through the instrument.

DESCRIPTION OF THE PREFERRED EMBODIMENT

In the attached Figures is illustrated a preferred embodiment of a hand-held instrument for evaluating any angular deviation of a line between selected points on a subject and a gravity-dependent reference line. Two gravity-dependent reference lines are provided by the illustrated embodiment: true vertical and true horizontal. While the illustrated embodiment is particularly useful in evaluating the posture of human subjects, it can also be used in other applications where it is desirable to determine the deviation of a line from true vertical or true horizontal.

As shown in FIG. 1, the hand-held instrument 10 has two major components: a transparent base 12 through which selected points on a subject may be viewed; and, a gravity-dependent indicator 14 mounted on the base on an axle 15 for free rotation under the influence of gravity. In the illustrated embodiment, the gravity-dependent indicator is also transparent. Both the illustrated base 12 and indicator 14 are preferably made of any suitable rigid, transparent plastic material (such as Plexiglas) approximately one-quarter inch in thickness.

The illustrated base 12 generally comprises a flat face 16 which is generally square-shaped with rounded corners. The base 12 includes a handle 18 parallel to the plane of the flat face 16 and extending outward from the center of one side of the face. The handle 18 has a central layer 20 integral with the face 16 and sandwiched between additional layers 22 adhered to the central layer 20 and having beveled edges for comfort in holding the instrument.

The base 12 also includes indicia 24 complementary with the gravity-dependent indicator 14 to provide an indication of the degree of deviation between the gravity-dependent indicator 14 and the selected points on the subject when the instrument is held in a substantially upright position. In the illustrated embodiment, the indicia include first 26 and second 28 fixed reference lines intersecting the axle 15, and angular division markings 30 (preferably marked in degrees) disposed in an arc about the axle 15.

The fixed reference lines 26, 28 are perpendicular to each other and extend to the edges of the face 16 of the base. The illustrated fixed reference lines are etched into the underside of the base, and darkened for ease of viewing. The angular division markings 30 are disposed in a circle near the edges of the face 16, and are marked off in degree increments around the circle with reference numerals disposed at intervals around the circle. The 0, 90, 180 and 270 degree markings are intersected by the fixed reference lines 26, 28.

The angular division markings 30 may be etched directly into the base 12. However, inasmuch as precision is required only in aligning the markings 30 to the axle 15, for reduced cost the markings 30 may be printed on a clear plastic material which is then adhered to the face 16 of the base 12.

The gravity-dependent indicator 14 includes a triangular-shaped vertical indicating pointer 32 extending radially from the axle 15 to a tip 34. The other part 36 of the indicator 14 is integral with the pointer 32, and is semi-circular in shape. A vertical indicating line 38 is etched into the top surface of the indicator 14 and extends from the tip 34 of the pointer 32, intersects the axle 15, and extends from the axle 15 to the opposite edge of the semi-circular part 36 of the indicator. The center of gravity of the indicator 14 lies along this line 38 in the semi-circular part 36 of the indicator 14 so that, when the instrument 10 is held upright, the indicator 14 will rotate on the axle 15 under the influence of gravity until the vertical indicator line 38 is at true vertical.

To provide a complementary indication of true horizontal when the instrument 10 is held upright, the weighted part 36 of the gravity-dependent indicator 14 has top edges 40 perpendicular to the vertical indicator line 38 and collinear with the axle 15.

The gravity-dependent indicator 14 is sized so that the tip 34 of the pointer 32 and the outer ends of the top edges 40 of the weighted part 36 intersect the angular division markings 30 so that angles can be easily read. Of course, as will be understood by a skilled artisan who has gained an understanding of the present invention, the particular shape shown for the indicator 14 in the illustrated embodiment is not critical to the invention, and other shapes may be chosen for this element.

Preferably, the gravity-dependent indicator 14 is mounted on the axle 15 for free rotation under the influence of gravity, with minimal interference from friction. It is also desirable that the gravity-dependent indicator be spaced from the face 16 of the base 12 in a parallel plane, to minimize possible interference with the rotation of the gravity-dependent indicator 14. To achieve these ends, a plurality of bearings and washers are provided in the illustrated embodiment.

Specifically, as best seen in FIG. 2, the axle 15 comprises a bolt, one end of which is threaded and has a reduced diameter. The axle bolt extends through a bore 42 in the gravity-dependent indicator 14 and through a second bore 44 in the base 12. The bores 42, 44 in the base 12 and indicator 14 contain bushings 46 with needle bearings 48 around their inner diameters to allow the axle bolt to rotate relatively freely therein.

Additional bearings are also preferably provided between the face 16 of the base 12 and the indicator 14, and between the indicator and the head 50 of the axle 15. As shown in FIG. 2, a first annular anti-friction bearing 52 is sandwiched between a first pair of washers 54; the washers 54 bear against the face 16 of the base 12 and the side of the gravity-dependent indicator 14. A second annular anti-friction bearing 56 is sandwiched between a second pair of washers 58. The second pair of washers 58 bear against the other side of the gravity-dependent indicator 14 and the head 50 of the axle bolt. Both annular anti-friction bearings 52, 56 may also include radial needle bearings on both upper and lower surfaces.

The entire assembly of axle, bearings, washers and the indicator is mounted to the base by a nut 60 threaded onto the threaded end of the axle bolt, with an additional washer 62 between the nut and the base 12.

The instrument of the present invention may be used to evaluate a variety of points on a subject. To use the instrument of the present invention to determine the degree of deviation of a line between selected points on a subject from a gravity-dependent reference, the instrument 10 is held upright by holding the handle 18. The selected points on the subject are viewed through the transparent instrument, and one of the fixed reference lines 26, 28 is superimposed across aligned with) the selected points. The gravity-dependent indicator 14 is then allowed to rotate until true vertical is established, and the degree of angular deviation, if any, is determined by reading the angular division mark intersected by either the tip 34 of the pointer 32 or the horizontal edges 40 of the weighted part 36 of the indicator 14. If the selected points on the subject are vertically or horizontally aligned, then the fixed reference lines 26, 28 will be aligned with the overlying vertical indicating line 38 and top edges 40 of the gravity dependent indicator and no angular deviation from true vertical or true horizontal will be shown.

The method of using the instrument of the present invention is particularly useful in evaluating the posture of a subject. Posture evaluations may be made with respect to various aspects of the subject. For example, the instrument may be held upright, about five to ten feet away from the subject, with the front of the subject in view: points on the subject's ears may be selected, one of the fixed reference lines of the base placed over these points, and the angle read from either the tip of the vertical indicating pointer or from one of the horizontal edges.

The same process may be followed for the subject's shoulders and the iliac crest of the hips. With the back of the subject in view, an evaluation of spinal curvature may be made. If a deviation such as a bow or curve can be observed, then more exact measuring techniques may be employed to quantify the degree of deviation. With the side of the subject in view, points may be selected on the subject, such as the middle ear, acromial process, middle hip, middle knee and middle ankle; the fixed reference line on the base of the instrument may be placed over any two of these points and the any deviation from true vertical may be noted.

In addition, the symmetry of the subject's body mass may be generally evaluated with respect to true vertical.

An additional advantage of the present invention is that it can be used to evaluate a subject in motion. Posture can be analyzed while the subject is walking, running and performing sports.

Still other aspects, objects, and advantages of the present invention can be obtained from a study of the specification, the drawings, and the appended claims.

I claim:

1. A hand-held instrument for evaluating the posture of a human subject by viewing the subject through the instrument and determining the degree of angular deviation on a line between selected points on the body of the subject from a gravity-dependent reference, the instrument comprising;

a planar base having a transparent portion through which the selected points on the subject may be viewed; and a planar gravity-dependent indicator mounted on the base for free rotation under the influence of gravity, the gravity-dependent indicator lying in a plane substantially parallel to and spaced from the base and having a transparent portion through which the subject may be viewed, the transparent portion of the gravity-dependent indicator overlying the transparent portion of the base;

wherein the base includes base indicia complementary with the gravity-dependent indicator to provide an indication of the degree of angular deviation between the gravity-dependent indicator and the line between the selected points on the body of the subject when the instrument is held in a substantially upright position, the base indicia including a reference fixed with respect to the base which fixed reference may be aligned with the selected points on the body of the subject so that the posture of the subject may be evaluated by determining the degree of angular deviation of a line between the selected points on the body of the subject from the gravity-dependent reference based upon the degree of angular deviation of the fixed reference from the gravity-dependent reference.

2. The hand-held instrument of claim 1 further comprising an axle for mounting the gravity-dependent indicator on the base, wherein the gravity-dependent indicator includes a vertical indicating pointer extending radially from the axle outwardly to a tip, and has a center of gravity substantially coplanar with the axle and the pointer tip so that when the instrument is held in a substantially upright position, the fixed reference may be aligned with the selected points on the body of the subject and the gravity-dependent indicator will rotate under the influence of gravity in a plane substantially parallel to the plane of the base to provide an indication of true vertical for comparison with the fixed reference.

3. The hand-held instrument of claim 2 further comprising an annular anti-friction bearing disposed between the transparent base and the gravity-dependent indicator to support the gravity-dependent indicator above the transparent base for free rotation on the axle, and wherein the axle extends through the annular anti-friction bearing and is disposed between the pointer and the indicator center of gravity.

4. The hand-held instrument of claim 3 further comprising a pair of anti-friction bushings disposed in bores in the gravity-dependent indicator and the base, wherein the axle is mounted for free rotation through the anti-friction bushings.

5. The hand-held instrument of claim 3 further comprising a pair of washers between which the annular anti-friction bearing is disposed.

6. The hand-held instrument of claim 2 wherein the gravity-dependent indicator includes a horizontal indicator for indicating true horizontal when the instrument is held in a substantially upright position so that the posture of the subject may be compared to true horizontal.

7. The hand-held instrument of claim 2 wherein:
the base indicia includes
angular division markings disposed in an arc about the axle, and
the fixed reference comprises a fixed reference line for said markings, which line is disposed in line with the axle at the transparent portion of the base and which may be aligned with the points on the body of the subject; and wherein the pointer tip intersects the arc of the division markings at the end of the markings indicating the determined angular deviation when the instrument is held in a substantially upright position and the reference line is aligned with the points on the body of the subject for posture evaluation, so that any angular deviation of the fixed reference line from true vertical may be determined.

8. The hand-held instrument of claim 5 wherein the indicator includes a horizontal indicator perpendicular to the vertical indicting pointer and intersecting the angular division markings so that when the instrument is held in a substantially upright position and the fixed reference line is aligned with the points on the body of the subject for posture evaluation, the posture of the subject may be evaluated by determining any angular deviation of the fixed reference line from true horizontal.

9. A method for evaluating the posture of a human subject by determining the degree of angular deviation of a line between selected points on the body of the subject from a gravity-dependent reference, the method including the steps of:

providing an angular measuring instrument including
a planar base having a transparent portion through which the selected points on the body of the subject may be viewed, said base including a fixed reference line and an angle indicia, and
a planar gravity-dependent indicator mounted on an axle on the base for free rotation under the influence of gravity and including a vertical indicating pointer extending radially from the axle outwardly to a tip, said indicator having a center of gravity collinear with the axle and the pointer tip, wherein the fixed reference line is aligned with the axle and is disposed at the transparent portion of the base, holding the instrument in a substantially upright position;

viewing the selected points on the subject through the base of the hand-held instrument;

turning the base to align the fixed reference line with the selected points on the subject;

allowing the indicator to rotate under the influence of gravity;

determining the deviation angle from the particular angle indicia aligned with the pointer.

10. The method for evaluating posture of claim 7 wherein the vertical alignment of the body of the subject is evaluated by viewing the side of the body of the subject through the instrument, aligning the fixed reference line over selected points between the subject's head and feet, and determining the degree of angular deviation from true vertical of the fixed reference line.

11. The method for evaluating posture of claim 10 wherein a series of evaluations are performed and the selected points include the middle ear and the acromial process, the middle hip and the middle knee, and the middle knee and the middle ankle.

12. The method for evaluating posture of claim 7 wherein the horizontal alignment of the body of the subject is evaluated by aligning the fixed reference line over selected points between the subject's head and feet, and determining the degree of angular deviation from true horizontal of the fixed reference line.

13. The method for evaluating posture of claim 12 wherein a series of evaluations are performed and the selected points include points on the subject's ears, shoulders and hips.

14. The method for evaluating posture of claim 12 wherein the horizontal alignment of the subject's head is evaluated by aligning the fixed reference line over comparable points of the subject's ears and determining the degree of angular deviation from true horizontal of the fixed reference line.

15. The method for evaluating posture of claim 12 wherein the horizontal alignment of the subject's shoulders is evaluated by aligning the fixed reference line over comparable points of the subject's shoulders and determining the degree of angular deviation from true horizontal of the fixed reference line.

16. The method for evaluating posture of claim 12 wherein the horizontal alignment of the subject's hips is evaluated by aligning the fixed reference line over comparable points of the subject's hips and determining the degree of angular deviation from true horizontal of the fixed reference line.

17. The method for evaluating posture of claim 7 wherein the vertical alignment of the spinal column of the subject is evaluated by aligning the fixed reference line over selected points of the subject's spinal column and determining the degree of angular deviation from true vertical of the fixed reference line.

* * * * *